United States Patent
Barrass et al.

(10) Patent No.: US 7,425,220 B2
(45) Date of Patent: Sep. 16, 2008

(54) METHOD FOR THE COSMETIC TREATMENT OF HAIR AND IMPLEMENT FOR CARRYING OUT THE SAME

(75) Inventors: Paul Leslie Barrass, Camberley (GB); Philip Davies, Banstead (GB); Delyth Angharad James, Egham (GB); Dale P. Pixley, Newtown, CT (US); Richard L. McManus, Shelton, CT (US); Bryan P. Murphy, Loveland, OH (US); Stevan David Jones, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 934 days.

(21) Appl. No.: 10/294,734

(22) Filed: Nov. 14, 2002

(65) Prior Publication Data
US 2003/0135937 A1      Jul. 24, 2003

Related U.S. Application Data

(60) Provisional application No. 60/333,096, filed on Nov. 14, 2001.

(51) Int. Cl.
*A61Q 5/10* (2006.01)
(52) U.S. Cl. .............. 8/405; 8/406; 8/101; 8/107; 8/111; 132/202; 132/208
(58) Field of Classification Search .......... 8/405, 8/406, 107, 111, 101; 132/202, 208
See application file for complete search history.

(56) References Cited

U.S. PATENT DOCUMENTS

| 2,655,924 A | 10/1953 | Petitta |
| 2,819,721 A | 1/1958 | Zakon |
| 3,610,257 A | 10/1971 | Hall |
| 4,450,152 A | 5/1984 | Ona et al. |
| 4,672,983 A | 6/1987 | Nath et al. |
| 4,830,030 A | 5/1989 | Busch et al. |
| 5,146,937 A | 9/1992 | Lefebvre |
| 5,845,653 A | 12/1998 | Abercrombie |
| 5,860,431 A | 1/1999 | Abercrombie et al. |
| 5,881,736 A | 3/1999 | Turner et al. |

(Continued)

FOREIGN PATENT DOCUMENTS

AU       2002230903 A       12/2001

(Continued)

OTHER PUBLICATIONS

Australian Government Letter dated Nov. 16, 2005.

*Primary Examiner*—Eisa B Elhilo
(74) *Attorney, Agent, or Firm*—Melissa Krasovec; Idris N. McKelvey; Marianne Dressman

(57) ABSTRACT

A cosmetic method for treating strands of hair comprising the subsequent steps of: placing the strands of hair to be treated between two substrates on which a first and second compositions capable of reacting together are applied, and implement for the same. The implement for carrying out the method may comprise a first and a second substrates in the form of strips of material that may be folded over each other such that at least one section of the strands of hair to be treated is sandwiched between the first and second compositions.

13 Claims, 3 Drawing Sheets

U.S. PATENT DOCUMENTS

| | | |
|---|---|---|
| 5,931,168 A | 8/1999 | Abercrombie et al. |
| 6,073,635 A | 6/2000 | Todd |
| 6,153,570 A | 11/2000 | Decoster |
| 6,295,993 B1 | 10/2001 | Ouellette |
| 2001/0008917 A1 | 7/2001 | Craig et al. |

FOREIGN PATENT DOCUMENTS

| | | |
|---|---|---|
| EP | 0 275 707 B1 | 12/1987 |
| EP | 0 492 657 B1 | 12/1991 |
| EP | 0 574 156 A2 | 5/1993 |
| GB | 2242357 A | 10/1991 |
| JP | 63-051315 | 3/1988 |
| JP | 06-096499 B | 11/1994 |
| JP | 07-053330 A | 2/1995 |
| JP | 07-053331 A | 2/1995 |
| WO | WO 02/47632 | 6/2002 |

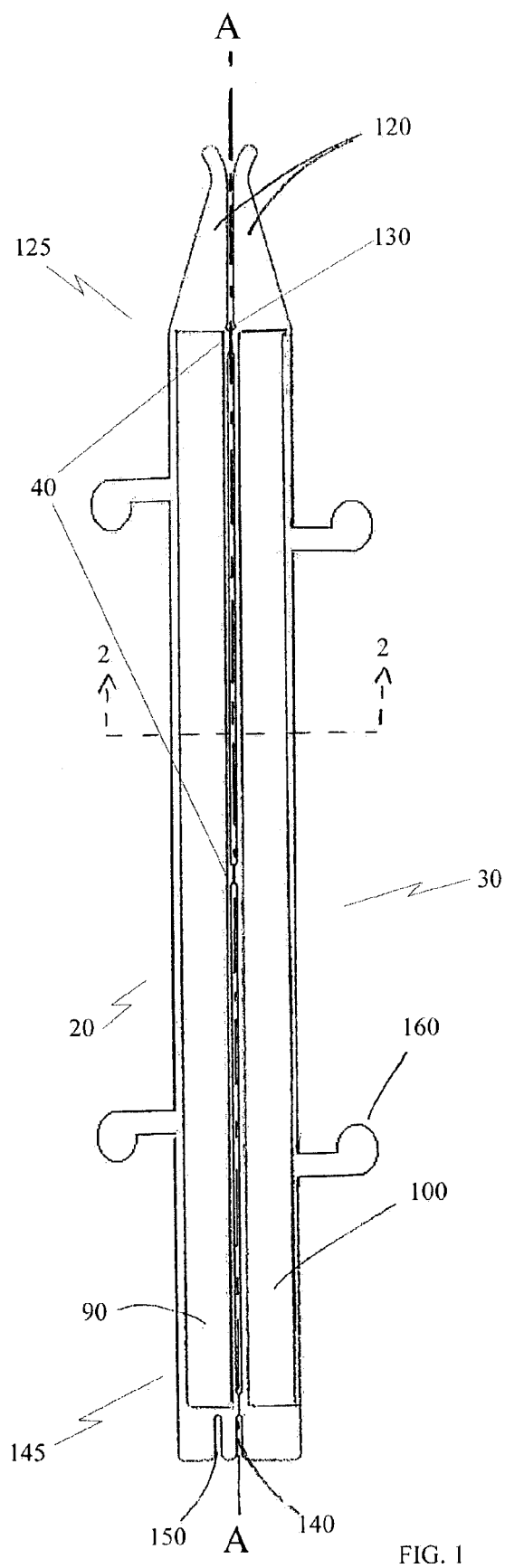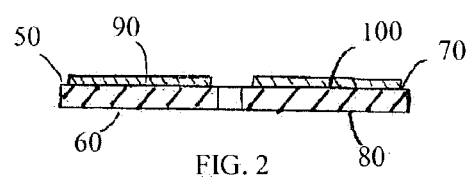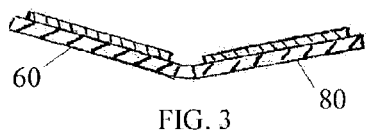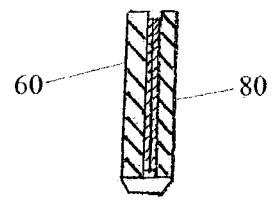

METHOD FOR THE COSMETIC TREATMENT OF HAIR AND IMPLEMENT FOR CARRYING OUT THE SAME

CROSS REFERENCE TO RELATED APPLICATION

This application claims the benefit under 35 USC 119(e) to U.S. application Ser. No. 60/333,096, filed Nov. 14, 2001.

BACKGROUND OF THE INVENTION

The present invention relates to a cosmetic treatment of hair, in particular highlighting, and an implement for carrying out the treatment.

Hair highlighting has been one of the mainstays of the professional salon industry. In this process, strands of hair are typically segregated from the remainder and treated with a composition comprising peroxides and/or persulfates. The technical skill required to separate the target hair and mix and apply decolorizing products to only those areas has kept this procedure mostly in the purview of hair salons. Traditionally, the segregation of hair was done by applying a plastic cap over the head and drawing small sections of hair through it. More commonly now, hair is selected through weaving and then placed onto metallic foils (usually aluminum foil) that are then painted with the highlighting composition. This allows for smaller, more independent sections to be treated, resulting in a more natural highlighted look. Although the effect is visually more appealing, these procedures are time consuming and generally require the skill of a professional haircolorist. Salons charge accordingly—often in excess of 100 USD per service.

Some highlighting services, especially on clients with lighter haircolor or those who desire less contrast in their highlights, are performed using oxidative haircolor techniques and products. These are performed using oxidative haircolor tints that have little or no oxidative dye precursors and are alkalized with relatively high levels of common hair dye alkalizers (generally, but not limited to, ammonium hydroxide and monoethanolamine). These are combined at the time of the service with high-volume peroxide developers to form an unstable highly alkalized peroxide composition that can effectively decolorize hair to a limited extent. By "high volume peroxide developer" we mean, as generally understood in the art of hairdressing, an aqueous peroxide solution, suspension, or emulsion that contains hydrogen peroxide in an amount greater than 30 volume (approximately 9.0% w/w). Higher levels of oxidative dye precursors (couplers and developers) in addition to the alkilizing agent may also be used if a further coloring effect is desired. In this case, the highlighted strands of hair will be at least partially colored by the oxidative dyes in addition to losing its natural shade due to the destruction of the natural pigments of hair (melanin) by the oxidizing agent. Therefore for the purpose of this application, the term "highlighting" encompasses "bleaching only" treatment and "bleaching plus dyeing" treatment (also referred to in the art as "permanent dyeing" or "permanent coloring").

Commonly, hair salons use high lift powdered bleaches for highlighting effects. High lift bleaches, using combinations of sodium, potassium, and ammonium persulfate along with hydrogen peroxide at elevated pH, provide fast decolorizaion with an acceptable amount of hair damage. Up to seven levels of lift are possible using a single application of some off-the-scalp bleaches. These are difficult to use due to the need to combine the persulfate mixture with the peroxide immediately prior to use. The high volume peroxide may be irritating to skin and mucous membranes. The persulfate powders are dusty and can be irritating if inhaled. This procedure is also limited by the technology in that the metallic foils need to be opened periodically to determine the degree of decoloration. Thus despite the high demand for these effects, high lift treatments are relegated to a small corner of the at-home consumer market.

Hydrogen peroxide solutions have been formulated into hair lightening products for consumer use. Products such as Sun In (RTM), A Touch of Sun (RTM), and most recently Salon Selectives Lighten Up Highlighting Mousse (RTM) have been introduced to give consumers a gradual highlighting effect. Hydrogen peroxide is unstable for storage at elevated pH (generally greater than pH 4.0) and the decolorizing effect of it at low pH is relatively weak. Therefore multiple applications of low pH products applied repeatedly over time are required to achieve a desired lightening effect. Further, these are whole-head lightening effects. Further examples of bleaching compositions are disclosed in U.S. Pat. No. 5,888,484 and U.S. Pat. No. 5,888,249.

As discussed above, highlighting usually involves mixing a first composition comprising an oxidizing agent and a second composition comprising an alkalizing agent and optionally oxidative dye precursors. The mixed composition should be carefully applied on the strands of hair to be treated so that it does not spread to adjacent sections of hair. In addition to the aluminum foil discussed above, various systems have been proposed for making sure that the composition remains on the strands of hair to be treated.

In U.S. Pat. No. 2,655,924 the strands of hair to be treated are pulled inside a tube using a hooked needle. A dyeing or bleaching composition is subsequently poured inside the tube, which is then sealed for the duration of the treatment.

U.S. Pat. No. 2,819,721 discloses another method of dyeing or bleaching hair wherein the hair to be treated is drawn in a first tube of deformable liquid-impervious material. The strands of hair are pulled inside the first tube of deformable material using a second tube movable within the first and having a jaw mechanism that can be actuated by the consumer. The first tube is subsequently filled with the treating composition.

U.S. Pat. No. 5,146,937 discloses the use of a sheet made of polymer material, preferably polystyrene, as a dye-applying pad for hair highlighting. The polystyrene sheet defines one and another opposite flat portions merging about a fold line. A lock of hair is laid over one flat half portion of the sheet, and a fluid dye solution including oxidizing means is applied to the lock of hair. The other flat half portion of the sheet is then folded over and flatly compressed against the first portion of sheet to take the locks in a sandwich for a sufficient development time to enable permanent hair coloring.

All these methods require the consumer to apply a fluid reactive composition to the hair to be treated, which can be messy and may require specialist training.

U.S. Pat. No. 5,845,653 and U.S. Pat. No. 5,931,168 disclose an applicator for transferring color-altering material from a rigid substrate to hair or fibers. The applicator includes a color-altering dye powder material soluble in water and/or water-activated which is affixed to at least one side of the applicator. The applicator is folded around the strands of hair to be treated and is activated by wetting either the hair or the applicator itself before use. These documents only consider applicators including one type of composition. Furthermore only powdered or particulate dyeing agents are considered.

U.S. 5,891,453 and 5,879,691 teach the use of strips of clear plastic coated with a hydrogen peroxide gel comprising a carbopol resin to whiten teeth.

U.S. 5,116,388 teaches the use of persulfate compositions enclosed in PVA packettes and their use in hair bleaching.

SUMMARY OF THE INVENTION

The present invention relates to cosmetic method for treating strands of hair comprising the subsequent steps of:
  a) providing a first substrate and a second substrate, wherein each substrate has an inner surface and an outer surface and wherein a first composition is applied on a region of the inner surface of the first substrate and a second composition is applied on a region of the inner surface of the second substrate,
  b) placing at least one section of the strands of hair to be treated between said first and second substrates such that at least one section of the strands is sandwiched between the first composition and second compositions,
  c) removing the first substrate and the second substrate from the hair.

The first composition and the second composition chemically react together to form a composition treating hair, for example a highlighting composition. The strands of hair may be left in contact with said inner surfaces during the time of the treatment. Alternatively the inner surfaces may be wiped along the strands of hair during step b).

The present invention also relates to an implement suitable for carrying out the method and which comprises:
  a) a first substrate having an inner surface and an outer surface, wherein a first composition is applied on said inner surface of said first substrate,
  b) a second substrate having an inner surface and an outer surface, wherein a second composition is applied on said inner surface of said second substrate,
  c) folding means for easily folding said first substrate over said second substrate such that at least on section of the strands of hair to be treated may be sandwiched between the first composition and the second composition.

The first and second compositions are capable, optionally after being activated, of reacting together to form a hair treating composition. This implement is especially suitable for highlighting selected strands of hair.

The first and second substrates can be made of the same material, for example a longitudinally divided woven or non-woven substrate wherein each of the compositions are applied on opposing halves. When folded, enclosing the targeted hair, the chemical compositions come into contact and react to form the effective treatment composition segregated from the remaining hair. The implement is preferably disposable and single use, so that each successive treatment uses a new implement.

BRIEF DESCRIPTION OF THE DRAWINGS

FIG. 1 is a front view of an embodiment of the implement according to the invention, said implement being in an open (non-folded position)

FIG. 2 is a cross sectional view of the embodiment of FIG. 1 along the line 2-2.

FIG. 3 is a cross sectional view of the embodiment of FIG. 1 along the line 2-2, said implement being in an intermediate folded position.

FIG. 4 is a cross sectional view of the embodiment of FIG. 1 along the line 2-2, said implement being completely folded.

DETAILED DESCRIPTION OF THE INVENTION

Figure 5:
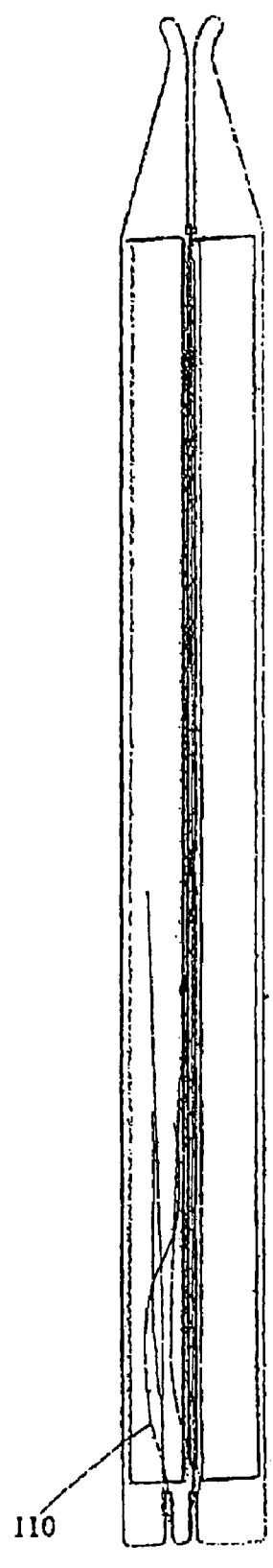
FIG. 5 is a front view of the embodiment of FIG. 1, the strands of hair being placed in said implement.

For the purpose of this invention, by "treatment of hair" or "method for treating hair" we mean as recognized by a beautician any of the common cosmetic hair treatments that require the mixing of two or more compositions. The compositions may chemically or physically react to form an active composition. The treatments include, but are not limited to, permanent or oxidative coloring, permanent waving, decolorizing processes such as: bleaching, highlighting, chunking, foiling etc. It will be obvious to those skilled in the art of cosmetic hair treatment that this invention has utility and advantages in other treatment modalities. It is also envisioned that other geometries of substrate can be used.

Throughout this description, a consumer may be any person who uses the method or the implements according to the invention. Some non-limiting examples: (a) in the case of a person who makes a personal use of the device, for example for highlighting their own hair or the hair of a friend or relative at home, the consumer is that person; (b) in the case of a person who goes to a salon or elsewhere to have a cosmetic product applied to their body by a beauty-care specialist, for example hair coloring by a hair care professional, that beauty-care specialist is the consumer; and (c) in the case of a person who dispenses a mixed product onto the coat of a pet or other animal, the consumer is that person.

Except as otherwise noted, all amounts including quantities, percentages, portions, and proportions, are understood to be modified by the word "about", and amounts are not intended to indicate significant digits. Except as otherwise noted, the articles "a", "an", and "the", mean "one or more". All documents cited are, in relevant part, incorporated herein by reference. The citation of any document is not to be construed as an admission that it is prior art with respect to the present invention.

As used herein the term "hair" to be treated may be "living" i.e. on a living body or may be "non-living" i.e. in a wig, hairpiece or other aggregation of non-living keratinous fibers. Mammalian, preferably human hair is preferred. However wool, fur and other keratin containing fibers are suitable substrates for the compositions according to the present invention.

As used herein, the term "applied" when referring to a composition is to encompass the terms coated, absorbed, adsorbed and adhered. Although the compositions are preferably applied directly to the substrate without an intermediate layer, an intermediate layer such a double-sided tape may be used in some cases to facilitate the adherence of the compositions to the substrate. Preferably the implement is sold with the compositions already applied on the substrate and "ready-to-use" by the consumer. It is possible for the consumer to apply one or both compositions on the implement before use, but this may render the method and implement more messy and less user-friendly.

Essential and optional elements of the methods and implements according to the present invention will now be described in detail by reference to various exemplary embodiments of the invention, several of which are also illustrated herein, wherein like numerals indicate the same elements throughout the description.

The Substrates

FIGS. 1-9 illustrate an embodiment of the implement according to the present invention which is generally indicated as 10. Implement 10 may be used to carry out the method according to the present invention, as is discussed hereinafter.

As shown on FIG. 1, implement 10 comprises a first substrate in the form of a strip of material 20 and a second substrate in the form of a strip of material 30. It is unimportant which is designated as a first substrate and which is designated as a second substrate. Bridges of material 40 along the line A-A connect the first and second substrate 20 and 30. The bridges are preferably thin (i.e. less than 2.5 mm thick). The implement 10 is preferably substantially elongated to accept various lengths of hair to be treated. Preferably the length of the substrates 20 and 30 is at least 5 cm, more preferably at least 10 cm, even more preferably at least 15 cm. The thickness of the substrates will depend on the material used and the type of compositions applied thereon. Typical thickness will range from 0.1 mm to 2.5 mm, preferably from 0.25 mm to 1.5 mm, more preferably from 0.5 mm to 1 mm.

The substrates may be formed from, but are not limited to, materials such as paper, plastic, fabric, rubber, metal foil, natural or synthetic woven or nonwoven material, polymeric films such as thermoplastic films of polyethylene or polypropylene, composite materials such as a coated nonwoven or a film-coated nonwoven material, a sponge, a cosmetic puff or any combinations thereof. Polymeric films are preferred, for example linear low, low, medium or high density polyethylene. Polymeric films may be easily extruded or cast and die cut to conform to the desired shape and dimensions of the substrates.

The materials that may be used for the substrates are preferably durable and disposable. They are preferably impervious to liquids and chemically compatible with the compositions used and are preferably manufactured from a thin plastic film, although other flexible liquid impervious materials may also be used. The substrates are preferably sufficiently flexible to be easily and safely applied to hair and sufficiently rigid to retain their shape during use, especially in a folded position. The materials forming the substrates may thus further be preferably described as:

- capable of supporting both compositions throughout storage and cosmetic application,
- impervious to liquids,
- not chemically reacting with either composition prior to or during application,
- sufficiently flexible to be easily and safely applied to hair and sufficiently rigid to retain its shape during use, and/or
- capable to be formed into a continuous looped tape.

The substrates may be preferably provided as clear or translucent to allow the operator to view the progress of the chemical treatment. The substrates may also comprise a specialized indicating agent that would indicate the progress of the reaction, for example by indicating changes in pH or RA (Reserve Alkanility).

The substrates may be partially or totally made of a water-soluble material (e.g. polyvinyl alcohol) such that upon rinsing they would either dissolve or be easily removed from the strands of hair on which they were applied.

Preferably both substrates and the folding means are made of the same material and are of unitary construction. The dimensions of the substrates may be tailored to the type of hair and/or treatment.

As shown on FIGS. 1-2, the first strip 20 comprises an inner surface 50 and an outer surface 60. Similarly, the second strip 30 comprises an inner surface 70 and outer surface 80. A first composition 90 is applied on the inner surface 50 and a second composition 100 is applied on the inner surface 70. It is preferred for the ease of manufacture of the implement that the first and second compositions are single products uniformly applied on their respective inner surface. However, as illustrated on FIG. 6 and FIG. 7 it is also possible to have additional compositions applied on the first or second substrate or both.

Figure 6:
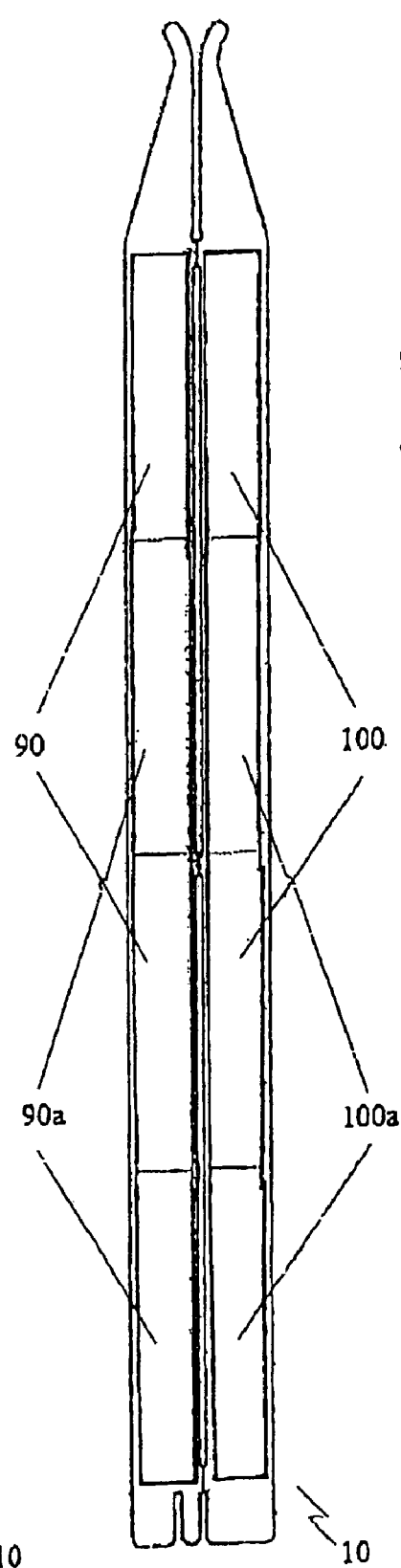
FIG. 6 is a front view of an embodiment of the implement according to the present invention wherein different compositions are applied in an alternating pattern on each substrate.

FIG. 6 illustrates an embodiment of the implement 10 wherein an additional composition 90a, having a formula similar to the second composition 100, is additionally applied to the inner surface of the first substrate and a composition 100a, having a formula similar to the first composition 90, is additionally applied to the inner surface of the second substrate, such that these additional compositions sandwich the strands of hair to be treated when the implement is in a folded position. "Similar compositions" means that the compositions have the same function (e.g. providing an oxidizing agent). Preferably similar compositions will have the same active and more preferably the same formula. The compositions 90, 90a may be applied on the inner surface of the first substrate according to an alternating pattern and the compositions 100, 100a applied on the inner surface of the second substrate may be applied complementarily, as illustrated on FIG. 6. In the case of a first composition comprising oxidative dye precursors and a second composition comprising an oxidizing agent, the "dye" compositions 90, 100a are brought in contact with the "oxidizing" compositions 90a, 100 when the implement is folded.

Figure 7:
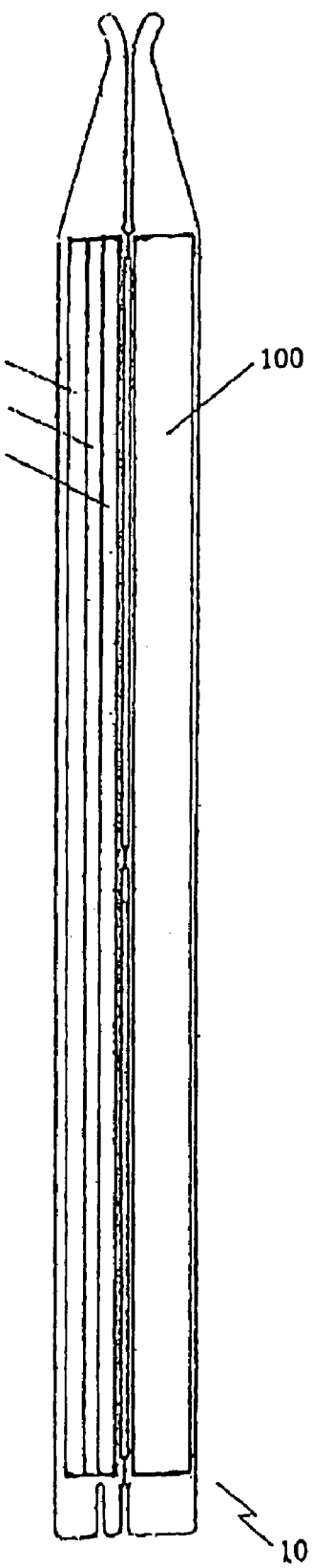
FIG. 7 is a front view of an embodiment of the implement according to the present invention wherein three different compositions are applied in the form of vertical stripes on the first substrate.

Another example of patterns is shown on FIG. 7, wherein three alternating vertical stripes of different compositions (90, 90b, 90c), which may be oxidative dye products, are applied on the first substrate. When the implement is folded, these vertical stripes are brought in contact with the second composition 100, which maybe an oxidizing product. More generally, one or more additional compositions may be applied on the inner surface of the first substrate, such that the strands of hair are sandwiched between said first composition and said additional composition(s) on one side and said second composition on the other side when the implement 10 is folded. The additional compositions also react with the second composition to form hair-treating compositions that treat the strands of hair. This configuration is well adapted to a first composition and additional compositions comprising oxidative dye precursors and a second composition comprising an oxidizing agent.

Preferably, the first and second compositions and any additional compositions are applied on more than 50%, preferably more than 60%, more preferably more than 75% of the total surface area of each of the first and second inner surfaces. For a given amount of composition, having the compositions applied on a relatively large surface of the substrates makes the implement more compact and therefore easier to handle.

Preferably however the inner surfaces of the strips may be provided with margins free from compositions along the edges of the inner surfaces. These margins allow the consumer to safely and easily handle the implement 10 without having to touch the compositions. As will be discussed below, these compositions may comprise potentially skin-irritating material such as hydrogen peroxide.

The inner surfaces of the substrates may be flat as shown in FIGS. 1-2.

The material making up the bridges 40 is sufficiently flexible for the implement 10 to be easily folded by the consumer along the line A-A as shown on FIGS. 2-4. The region 90 is preferably substantially symmetrical with the region 100, so that when the first strip is completely folded over the second strip as shown on FIG. 4, said first and second compositions are substantially in contact with each other and can react to form the treating composition at the surface of contact. This provides optimal use of the first and second compositions. A folding line embossed in a flexible strip of substrate and dividing said strip in to the two substrates according to the present invention may also serve as folding means.

Figures 8, 9:
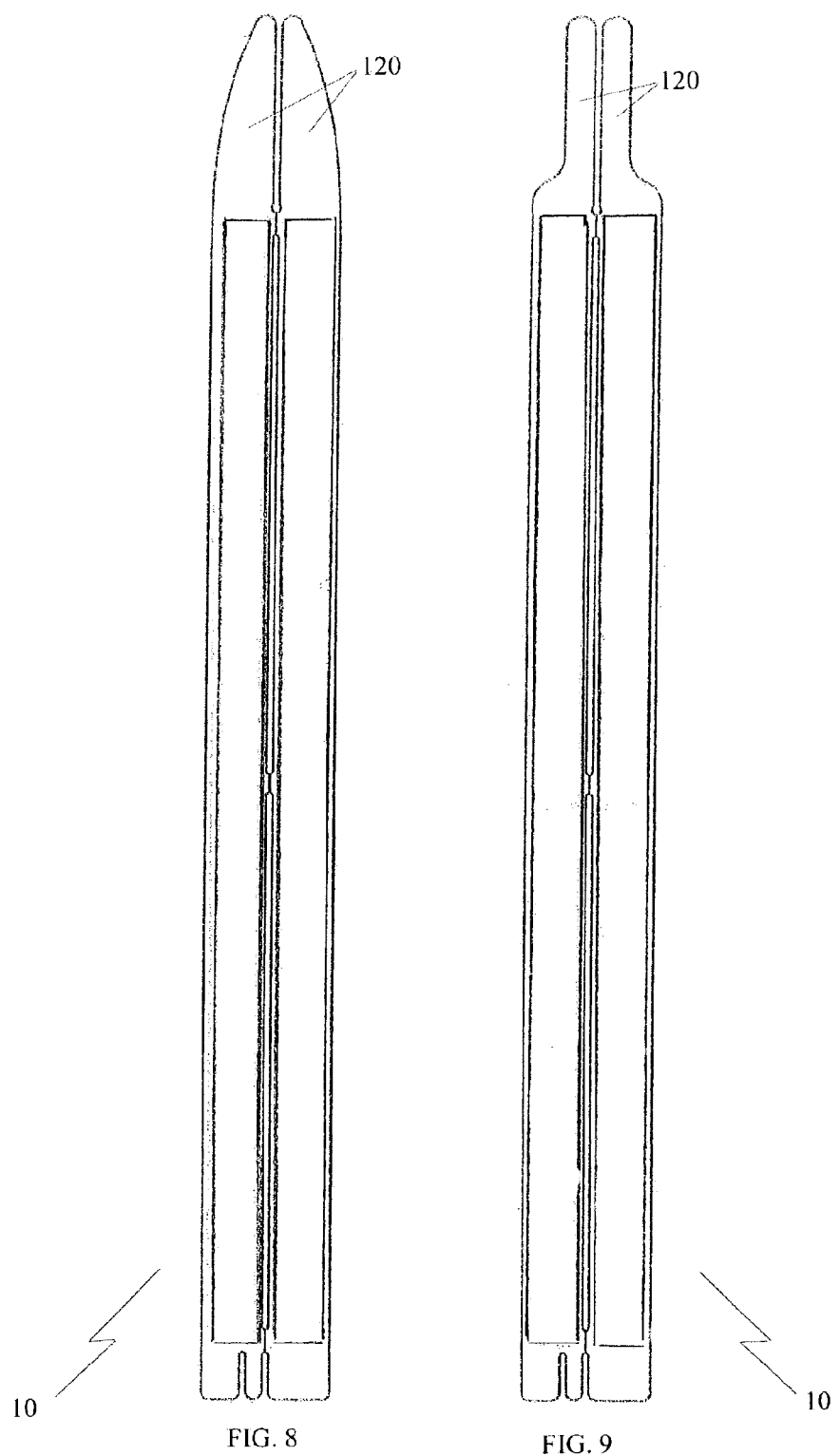
FIG. 8 is a front view of an embodiment of the implement according to the invention, with an alternative upper tip.
FIG. 9 is a front view of an embodiment of the implement according to the present invention, with a further alternative upper tip.

As shown on FIG. 5 the strands of hair 110 to be treated is placed between the strips 20 and 30 before folding these over each other. The strips may comprise plucking means 120 for facilitating the positioning of the hair between the two strips 20, 30. The plucking means helps the consumer to gather the strands of hair to be treated. As shown in FIGS. 1, 8 and 9, the plucking means may be, for example, formed on the top end 125 of the implement 10 by narrowing tips of the strips 20, 30 hat converge along the line A-A. These narrowing tips can be used as a scoop for plucking the strands of hair to be treated and inserting them between the strips 20, 30. A first recess 130 on the same top end of the implement 10 is provided for further facilitating the positioning of the strands of hair to be treated. A second recess 140 on a bottom end 145 of the implement 10 may be further provided. This second recess will be helpful if the strands of hair to be treated are longer than the strips 20, 30 and projects beyond the bottom end of the implement 10. In this case, the strands of hair will be inserted in the second recess to allow a stronger and more stable positioning of the strands of hair. When this second recess is complemented by a third, adjacent recess 150, longer strands of hair can be looped along these recesses and guided back up the strip to provide that the whole length of the hair is sandwiched between the folded strips. Although two recesses are drawn on FIG. 1, it is contemplated that a prong protruding beyond the end of the first strip would have the same effect and could be used similarly.

Preferably the consumer should not have to maintain a pressure to keep the implement in a folded position during the treatment, especially if the treatment lasts more than a few minutes. It is therefore preferred that the implement may comprise closing means for maintaining the first and second strips in a folded position during the treatment. If the first and second compositions are sufficiently sticky, the adhering forces between these compositions may be enough. Alternatively an adhesive may be provided in any margin of the inner surfaces, which are free of composition. Mechanical means may also be used, as shown of FIG. 1 where interlocking hooks 160 are distributed along the edges of the substrates. When the implement 10 is closed, these hooks can be placed in an interlocking position that allows the implement to remain in a folded position during the treatment. Preferably, the closing means should be easily releasable so that when the treatment is finished the implement can be easily removed from the strands of hair. If adhesives are used, these should be preferably of such a strength that both substrates can be easily manually unfolded.

The outer surfaces of the first and the second substrates may be provided with a further layer of material having functional or aesthetic properties. For example, this layer could provide a better grip, rigidity or appearance to the implement. This layer could support information about the type of treatment provided by the implement, such as words describing the treatments or colors indicating the end result of the treatment in case of a coloring treatment.

In instances where any of the compositions should be protected from air, it is preferred that the compositions are protected during storage by a release liner. The release liner may be formed from any material which exhibits less affinity for substance than the substance exhibits for itself and for the strip of material. The release liner preferably, but not necessarily, may comprise a rigid sheet of material such as polyethylene, paper, polyester, or other material which is then coated with a non-stick type material. The release liner material may be coated with wax, silicone, polyester such as Teflon (RTM), fluoropolymers, or other non-stick type materials. A preferred release liner is Scotchpak (RTM), produced by 3M. The release liner may be cut to substantially the same size and shape as the strip of material or the release liner may be cut larger than the strip of material to provide a readily accessible means for separating the material from the strip.

The release liner may be formed from a brittle material which cracks when the strip is flexed or from multiple pieces of material or a scored piece of material. Alternatively, the release liner may be in two overlapping pieces such as a typical adhesive strip bandage type design. A further description of materials suitable as release agents is found in Kirk-Othmer Encyclopedia of Chemical Technology, Fourth Edition, Volume 21, pp. 207-218, incorporated herein by reference.

The Compositions Applied on the Substrates

The first composition is capable of reacting with the second composition to form a hair treating composition. When the first and second compositions are brought into contact, the hair treating composition may be formed immediately or a further activation step may be required. For example the reaction may be heat-, water- or pressure-activated. In the case of water-activation, the hair could be wetted prior to being placed between the substrates or the substrates could be wetted prior to being applied on the strands of hair, or both.

The amount of substance applied on the substrates will depend upon the size and capacity of the piece of material, concentration of the actives, and the desired end results.

In a preferred embodiment, the hair treating composition formed by the first and second compositions will be a composition suitable for highlighting hair, optionally comprising oxidative dye precursors for coloring the hair.

Examples of compositions that may be applied on the first or second substrate are discussed below. It is unimportant which is designated as first composition and which is designated as second composition. The compositions according to the present invention can be provided in any form for highlighting hair and/or coloring hair, such as an aqueous composition, a paste, a viscous liquid, a powder, a gel or an oil-in-water emulsion. Preferred media for the compositions according to the present invention are thickened solutions comprising a salt-tolerant thickener or oil-in-water emulsions. Preferably the compositions applied on the substrates are in the form of a gel, which provides good adhering properties to the products and a source of water that may facilitate the mixing of the reactants comprised in the first and second compositions. Hydrogels are especially preferred.

As discussed above, an activation step may be required to initiate reaction between the first and second compositions. In a further, alternate, embodiment, an activation step may be required in order to bring the first and second compositions in contact with other. For example, pressure-activation may take place if the compositions are trapped in plastic bubbles that are easily frangible, such as polyethylene or polypropylene "CARMA" bubbles, supported by a backing made of a plastic material. "CARMA" stands for "Consumer Activated Rupturable Multi-cell Applicators", a film technology for delivering product to a surface, consisting of product trapped in closed cells, which when ruptured deliver the trapped product to the surface. The bubbles would be burst, and the products that they contain released, by applying a sufficient amount of pressure on the outer surfaces of the substrates. The compositions contained in the bubbles would then mix, permitting them to form the treating composition.

The compositions may also comprise a water-soluble material (e.g. PVA) that would dissolve upon rinsing, thus facilitating the release of the implements when the treatment is finished.

EXAMPLES OF COMPOSITIONS

The compositions below are exemplary composition that may be applied on the first or second substrates.

Example 1

Hydrogen Peroxide Composition

An exemplary hydrogen peroxide composition that may be applied on the first or second substrates may comprise the following:
 1. Water, 5-95%,
 2. Thickening Agent, 0.1-20%,
 Preferred thickening agents are chosen from polymers (including gelling agents), gel phases referred to as creams or emulsions and combinations thereof.
 Suitable polymers may be selected from carboxymethyl cellulose, carboxypropyl cellulose, carboxypolymethylene (Carbomers, Carbopols e.g. Carbopol ETD 2020, all RTM), carboxyvinyl Polymers, poloxamers, polyethylene glycol, natural gums (including but not limited to carrageenan, tragacanth, karaya, arabic, guar and xanthan), natural and synthetic smectite clays (including but not limited to hectorites, bentonites and montmorillonites), scleroglucan, methyl cellulose, ethyl cellulose (commercially available as Aquacote (RTM)), hydroxyethyl cellulose (hydroxypropylmethyl cellulose, microcrystalline cellulose, hydroxybutylmethyl cellulose, hydroxypropyl cellulose (Klucel (RTM)), hydroxyethyl ethyl cellulose, cetyl hydroxyethyl cellulose (Natrosol (RTM) Plus 330), N-vinylpyrollidone (Povidone (RTM)), Acrylates/Ceteth-20 Itaconate Copolymer (Structure (RTM) 3001), hydroxypropyl starch phosphate (Structure (RTM) ZEA), polyethoxylated urethanes or polycarbamyl polyglycol ester (e.g. PEG-150/Decyl/SMDI copolymer=Aculyn (RTM) 44, PEG-150/Stearyl/SMDI copolymer=Aculyn 46 (RTM) ), trihydroxystearin (Thixcin (RTM)) acrylates copolymer (e.g. Aculyn (RTM) 33) or hydrophobically modified acrylate copolymers (e.g. Acrylates/Steareth-20 Methacrylate Copolymer=Aculyn (RTM) 22).
 A representative but not exhaustive list of polymers and thickening agents can be found in "The Encyclopaedia of Polymers and Thickeners for Cosmetics" compiled and edited by Robert Y. Lochhead, phD and William R. Fron, Department of Polymer Science, University of Southern Mississippi
 Suitable gel phase referred to as creams or emulsions may be selected from cetyl alcohol, stearyl alcohol, fatty acids and mixtures thereof.
 3. Hydrous Peroxide Compound, 0.1-35%,
 For example cosmetically acceptable peroxide producing compounds, including but not limited to: peroxides (hydrogen, calcium, carbonates (e.g. sodium, ammonium, potassium), carbamides, alkaline earth, inorganic alkali metal peroxides (e.g. sodium periodate, sodium peroxide), organic peroxides (e.g. urea peroxide, melamine peroxide), inorganic perhydrate salt bleaching compounds (e.g. alkali metal salts of perborates, percarbonates, perphosphates, persilicates, persulphates) etc.
 4. Optionally glycerine, 1-50%.
 The composition is preferably in the form of a gel.

Example 2

Peroxygen Generator Blend

An exemplary peroxygen generator blend composition that may be applied on the first or second substrates may comprise the following:
 1. Peracid compound, typically 1-60%.
 Suitable peracid compounds may be persulfates (e.g. ammonium, potassium and/or sodium salts), percarbonates (e.g. ammonium, potassium and/or sodium salts), carbonates (e.g. ammonium, potassium and/or sodium salts), perhydrates (e.g. citric acid, sodium phosphate and/or sodium carbonate salts) and mixtures thereof.
 2. Hydroxides (e.g. ammonium, potassium and/or sodium salts), typically 0.1-8%
 3. Silicates: sodium, sodium meta-, typically 0.1-20%,
 4. Surfactant: sodium lauryl sulfate (Dry Powder), typically 0.1-5.0%,
 5. Silica, q.s.

Example 3

Alkalizing Composition

1. Water, typically 5-99%,
 2. Thickening agent, typically 0.5-20%,
 Preferred thickening systems are chosen from the same list as already discussed for the hydrogen peroxide composition.
 3. Cosmetic Alkalizer, typically 0.1-20%
 Preferred are any or combinations of the common alkalizing agents used in cosmetic manufacture, including but not limited to hydroxides (e.g. ammonium, potassium and/or sodium salts), ethanolamines (e.g. mono-, di- and/or tri-), isopropanolamines, aminomethulpropanol, carbonates (e.g. sodium, ammonium, potassium),
 4. optionally dyes, including oxidative dye precursors or direct dye.
 The alkalizing composition is preferably in the form of a gel.

Other Ingredients

Moreover, it is also intended that the compositions of the present invention may comprise other components that may or may not be active ingredients. This includes, but is not limited to, additional colorants (temporary, semi-permanent, demi-permanent, or permanent and also either natural or synthetic), chelants (e.g. ethylene diaminedissucinnic acid) buffering agents, thickeners, solvents, enzymes, anionic, non ionic, amphoteric and/or cationic surfactants, conditioning agents, carriers, antioxidants, stabilizers, perming actives, perfume, hair swelling agents, hair straightening agents. Some of these additional components are detailed hereafter.

Oxidative Dye Precursors

These compounds include aromatic diamines, aminophenols and their derivatives (a representative but not exhaustive list of oxidation dye precursor can be found in Sagarin, "Cosmetic Science and Technology", "Interscience, Special Edn. Vol. 2 pages 308 to 310). Precursors can be used with couplers. Couplers are generally colorless molecules that can form colors in the presence of activated precursors.

The choice of precursors and couplers will be determined by the color, shade and intensity of coloration that is desired. The precursors and couplers can be used herein, singly or in combination, to provide dyes having a variety of shades.

The hair dye component of a hair dye compositions will generally comprise from 0.001% to 10%, preferably from 0.1% to 3%, of oxidative dye precursors and couplers.

Conditioning Agent

The compositions of the present invention preferably, but not necessarily, further comprise at least one conditioning agent. Preferred conditioning agents are selected from silicone materials, especially nonvolatile silicone and amino functionalised silicones, cationic surfactants, cationic polymers and mixtures thereof.

The conditioning agent will generally be used at levels of from 0.05% to 20% by weight of the composition, preferably of from 0.1% to 15%, more preferably of from 0.2% to 10%, even more preferably of from 0.2% to 2%. The minimum level that is used in a particular composition should be effective to provide a conditioning benefit. The maximum level that can be used is not limited by theory, but rather by practicality. It is generally unnecessary and expensive to use levels in excess of about 20%.

Suitable conditioning agents are disclosed in WO9804237 p.22-p.29, and in WO9632919 p.17-22, both incorporated herein by reference.

EXAMPLES OF HIGHLIGHTING PROCESSES

Three highlighting processes are described—two using a hydrogen peroxide composition and an alkalizing gel, the last using a hydrogen peroxide composition and mixed persulfates.

Example A

Hair Decolorizing Using Gelled Peroxide and Gelled Alkalizer

A decolorizing composition that is useful for a hair highlighting consumer who desires only a small amount of lift (decolorizing) would not require the powerful peracid chemicals. This example teaches the production of a hair highlighter using gels of peroxide and a suitable cosmetic alkalizer. The compositions of the example are as follows:

| Ingredients | % w/w |
| --- | --- |
| Composition 1 - Peroxide Gel | |
| De-ionized Water | q.s. to 100% |
| Glycerine | 5.00 |
| Hydrogen Peroxide (50% Active) | 12.50 |
| Carbomer | 0.60 |
| Sodium Hydroxide (45% aq. Solution) | q.s. to pH 5.0 |

| Ingredients | % w/w |
| --- | --- |
| Composition 2 - Alkalizer Gel | |
| De-ionized Water | q.s. to 100% |
| Ammonium Hydroxide (45% Active) | 4.00 |
| Carbomer | 0.25 |

The first composition is produced by combining the Carbomer with the glycerine and mixing until a homogenous slurry is obtained. De-ionized water is charged into a separate container of sufficient size to contain the entire batch. The slurry is introduced into the water slowly and mixed with moderate agitation until a stable, homogenous gel is observed. Hydrogen peroxide is then added with moderate mixing so as not to introduce excess air bubbles into the system. Then, sodium hydroxide is added dropwise to increase the pH to approximately 5.0—activating and gelling the carbomer. Optionally, additional peroxide stabilizers such as sodium stannate may be added to further reduce the likelihood of premature peroxide decomposition.

The second composition may be produced by hydrating the Carbomer in rapidly mixing water—either by slow manual addition (so as not to produce "fisheyes" of undispersed polymer)—or by using an eductor or similar device for rapid hydration of powders. When the carbomer is fully dispersed and homogenous add the Ammonium Hydroxide with moderate mixing so as to avoid entrapping excess air bubbles. The batch will thicken and clear with the addition of the alkalizer.

A clear polyethylene film substrate approximately 20 cm long by 6 cm wide may be divided in half and folded so as to make a double sheet 3 cm wide. The thickness of the film is about 1 mm. A layer of composition 1 approximately 0.4 mm thick is applied to an inside surface on one half of the clear polyethylene film. Opposite of that, book style, a layer of composition 2 of similar thickness is applied to the polyethylene film. A section of human hair (Caucasian Dark Brown—International Hair Imports and Products, Valhalla, N.Y.) approximately 2 cm wide (slightly narrower than the folded polyethylene strip) and approximately 0.4 mm is segregated from the remaining hair within the strip. The chemically treated halves of the strip are compressed together around the hair. The hair is allowed to process within the strip for 45 minutes at ambient temperature or under a hood type hair dryer for a shorter time.

Example B

Gelled Peroxide and Gelled Alkalizer Comprising Oxidative Dye Precursors

A second preferred method of this invention may be to use a divided substrate treated on one side with a hydrogen peroxide gel and on the other side with an alkaline gel containing oxidative dye precursors. In this example the simultaneous bleaching of the underlying substrate colour and deposition of dyes will result in a mid brown shade.

The compositions of the example are as follows:

| Ingredients | % w/w |
| --- | --- |
| Composition 1 - Peroxide Gel | |
| De-ionized Water | q.s. to 100% |
| Glycerine | 5.00 |
| Hydrogen Peroxide (50% Active) | 12.50 |
| Disodium EDTA | 0.04 |

-continued

| Ingredients | % w/w |
| --- | --- |
| Carbomer | 0.60 |
| Sodium Hydroxide (45% aq. Solution) | q.s. to pH 5.0 |
| Composition 2 - Oxidative Dye + Alkalizer Gel | |
| De-ionized Water | q.s. to 100% |
| Ammonium Hydroxide (45% Active) | 4.00 |
| Carbomer | 1.00 |
| Glycerine | 5.00 |
| Sodium Sulphite | 0.10 |
| EDTA | 0.05 |
| Erythorbic acid | 0.40 |
| Para-phenylenediamine | 0.76 |
| Citric Acid | 0.40 |
| N,N-Bis(2-Hydroxyethyl)-P-Phenylenediamine | 0.41 |
| Resorcinol | 0.40 |
| 1-Napthol | 0.01 |
| m-aminophenol | 0.02 |
| Phenyl Methyl Pyrazolone | 0.10 |
| Toluene-2,5-diamine Sulphate | 0.076 |
| Trisodium Ethylenediamine Disuccinate | 6.7 |

The first composition may be produced by combining the carbomer with the glycerine and mixing until a homogenous slurry is obtained. De-ionized water is charged into a separate container of sufficient size to contain the entire batch. The slurry is introduced into the water slowly and mixed with moderate agitation until a stable, homogenous gel is observed. Hydrogen peroxide is then added with moderate mixing so as not to introduce excess air bubbles into the system. Finally sodium hydroxide is added dropwise to increase the pH to approximately 5.0—activating and gelling the carbomer. Optionally, additional peroxide stabilizers such as sodium stannate may be added to further reduce the likelihood of premature peroxide decomposition.

The second composition is produced by hydrating the carbomer in rapidly mixing water—either by slow manual addition (so as not to produce "fisheyes" of undispersed polymer)—or by using an eductor or similar device for rapid hydration of powders. When the carbomer is fully dispersed and homogenous add all the remaining ingredients, apart from ammonium hydroxide (i.e. glycerine, dye precursors, pH buffers and antioxidants). Once they have dissolved, the ammonium hydroxide is added with moderate mixing so as to avoid entrapping excess air bubbles. The batch will thicken and clear with the addition of the alkalizer.

The substrates may be prepared as in example A.

Example C

Hair Decolorizing Using Persulfates and Peroxide

A third preferred method of this invention is to use a divided substrate treated on one side with a persulfate bleach mixture similar to the professional salon product Basic White Dedusted Highlighting Bleach (RTM) opposite a concentrated hydrogen peroxide gel. This may provide a high level of decolorizing effect in a short amount of time and with an acceptable degree of hair damage. As persulfate bleaches are typically sold in the form of a blended anhydrous powder, a method of immobilizing the powder mixture may be required. Hydrogen peroxide, a cosmetic oxidizer, maybe sold as a water-thin liquid solution and may be immobilized for use within the scope of the invention.

Powdered compositions of persulfates may be more difficult to immobilize. Although soluble in water, persulfates typically decompose rapidly and exothermically upon hydration. Therefore conventional aqueous gelling agents are typically not suitable for use. Anhydrous slurries, pastes and creams of persulfates in oils, waxes and/or silicones do exist (see Wella patent below), but may be less desirable for use in this invention, unless their hydrophobic nature is overcome. These typically do not readily mix with gelled peroxide upon simple contact. Decolorant slurries adsorbed within a textile as described in U.S. Pat. No. 5,888,249 provide a method to immobilize ammonium carbonate, but have not been proven to work with the preferred persulfates.

A method of persulfate immobilization described in U.S. Pat. No. 5,116,388 is to package the powder in small pockets of polyvinyl alcohol (PVA) films, adhered to a plastic substrate. In this way a measured dose of persulfate composition can be safely and cleanly adsorbed onto the supporting substrate and remain separated from the peroxide composition. Such PVA films are readily soluble in the peroxide gel. Upon contact with the peroxide gel, the PVA dissolves and the persulfate blend mixes with the peroxide gel to for the decolorizing composition. To further enhance the mixing, a small amount of a salt, preferably sodium chloride, can be added to either the persulfate mixture or applied to the exterior surface of the PVA film. Upon contact with the salt, the peroxide gel will typically quickly lower in viscosity and more readily flow into and mix with the persulfate blend.

The compositions of the third example are as follows:

| Ingredients | % w/w |
| --- | --- |
| Composition 1 - Peroxide Gel | |
| De-ionized Water | q.s. to 100% |
| Glycerine | 5.00 |
| Hydrogen Peroxide (50% Active) | 12.50 |
| Carbomer | 0.60 |
| Sodium Hydroxide (45% aq. Solution) | q.s. to pH 5.0 |
| Composition 2 - Peroxygen Generator Blend | |
| Silica | q.s. to 100% |
| Ammonium Persulfate | 20.0 |
| Potassium Persulfate | 35 |
| Sodium Persulfate | 5.0 |
| Sodium Metasilicate | 10.0 |
| Sodium Lauryl Sulfate | 1.0 |
| Sodium Chloride | 0.25 |

The first composition may be produced by combining the carbomer with the glycerine and mixing until a homogenous slurry is obtained. De-ionized water is charged into a separate container of sufficient size to contain the entire batch. The slurry is introduced into the water slowly and mixed with moderate agitation until a stable, homogenous gel is observed. Hydrogen peroxide is then added with moderate mixing so as not to introduce excess air bubbles into the system. Then, sodium hydroxide is added dropwise to increase the pH to approximately 5.0—activating and gelling the Carbomer. Optionally, additional peroxide stabilizers such as sodium stannate may be added to further reduce the likelihood of premature peroxide decomposition.

The second composition is produced by the dry blending of all of the dry ingredients, in any order, in a suitable blending apparatus such as a V-blender. The composition should be combined to homogeneity by whatever blending means are chosen.

Approximately 5 grams of the blended persulfate composition is then poured into a 10 cm by 3 cm packet made of dried PVA polymer films. This is heat sealed so as to exclude moisture until the time of use. The packet is adhered to one side of the divided support substrate using double-sided transparent adhesive tape. The peroxide gel of composition 1 is applied to the opposing side of the support substrate in the same manner as the previous example.

As in example A, during treatment the hair is segregated within the folded substrate causing the peroxide gel and the persulfate packet to come into contact. In this embodiment of the invention it is advantageous that the hair be wet so as to accelerate the dissolution of the PVA packet allowing the two compositions to react more quickly. The hair is then treated with these compositions for 15-60 minutes, more preferably from 25-45 minutes or until sufficient decolorization of the hair is achieved.

Other Advantages and Variations of the Present Invention

The method and implements according to the present invention may be used in combination with an all-over treatment of the hair. For example, a previous hair treating composition (e.g. hair coloring) could previously be applied to the whole of the hair and then followed by the applications of the implements of the present invention. This would have the advantage of, at the same time, giving grey coverage or changing the color of the rest of the hair whilst highlighting selected strands of hair. Alternatively, the implements could be previously applied to strands of hair and while still on the head, a further treating composition (coloring) could be applied to the remainder of hair, with the same advantages as above.

The implements can be sold separately or in a package comprising several implements. In the latter cases, the implements can all be the same (same treating composition), or different (for example to achieve different type of color highlight). The implements may be packaged individually in a sealed package.

The implements could also be sold in bulk rolls for the professional market from which sections would be cut according to length or width of hair to be treated. Rolls or individual implements may be serrated vertically and/or horizontally to tailor them to the consumer needs (e.g. length of hair and thickness of highlight required). Other morphologies are also envisioned. For instance, a nested two-piece highlighting cap, with one composition on the outer surface of the inner cap (through which the hair is pulled) and the complimentary composition on the inner surface of the external cap. The hair to be treated would be sandwiched between the two caps during processing.

Figure 10:
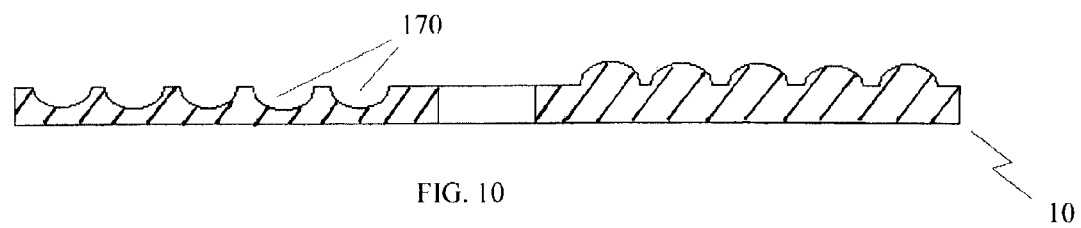
FIG. 10 is a cross sectional view of an embodiment similar to the embodiment of FIG. 1 but comprising several grooves for simultaneously treating several strands of hair.

The substrates may also comprise grooves or ridges for simultaneously treating several locks of hair as shown in FIG. 10. Each individual groove 170 may or may not comprise a composition. For example, it is possible to automatically segregate locks of hair into composition and non-composition containing regions. A single composition or different compositions may be applied in the compositions-containing grooves.

What is claimed is:

1. A method for treating strands of hair comprising the subsequent steps of:
   a) providing a first substrate and a second substrate, wherein said first and second substrates are impervious to liquids, wherein the first substrate has an inner surface and an outer surface and the second substrate has an inner surface and outer surface, and wherein a first composition is applied on the inner surface of the first substrate and a second composition is applied on the inner surface of the second substrate,
   b) placing at least one section of the strands of hair to be treated between said first and second substrates and folding said first substrate over said second substrate such that said at least one section is sandwiched between said first composition and said second composition,
   c) removing the first substrate and the second substrate from the strands of hair, characterized in that said first and second compositions react together to form a hair treating composition that treats the strands of hair during step b).

2. A method according to claim 1 wherein the first composition comprises an alkalizing agent and the second composition comprises an oxidizing agent, and wherein said hair treating composition is a hair highlighting composition.

3. A method according to claim 2 wherein said first composition further comprises oxidative dye precursors.

4. A method according to claim 1 wherein the strands of hair are kept in contact with said inner surfaces during the time of the treatment.

5. A method according to claim 1 wherein the reaction between the first composition and the second composition is activated.

6. A method according to claim 5 wherein the activation mechanism is selected from the group consisting of heat-, water- and pressure-activation.

7. A method according to claim 1 wherein the substrates have substantially the same shape.

8. A method according to claim 1 wherein both substrates are made of a strip of flexible material.

9. A method according to claim 1 wherein the first composition and the second composition are in a form selected from the group consisting of aqueous composition, paste, viscous liquid, powder, oil-in-water emulsion and gel.

10. A method according to claim 1, wherein a composition similar to the first composition is additionally applied on the inner surface of the second substrate and a composition similar to the second composition is additionally applied on the inner surface of the first substrate, such that at least one section of the strands of hair to be treated is sandwiched between said additionally applied compositions during step b).

11. A method according to claim 10 wherein the compositions are applied on the inner surface of the first substrate according to an alternating pattern and the compositions applied on the inner surface of the second substrate are applied complementarily.

12. A method according to claim 1 wherein at least one additional composition is applied on the inner surface of the first substrate, such that at least one section of said strands of hair is sandwiched between said first composition and said at least one additional composition on one side, and said second composition on the other side, and wherein said at least one additional composition also reacts with the second composition to form at least one additional hair treating composition that treats the strands of hair during step b).

13. A method according to claim 12 wherein said first composition and said at least one additional composition comprises an alkalizing agent and said second composition comprises an oxidizing agent, and wherein said hair treating composition and said additional hair treating composition are hair highlighting compositions.

* * * * *